United States Patent [19]

Barberich et al.

[11] Patent Number: 5,571,827
[45] Date of Patent: Nov. 5, 1996

[54] METHODS AND COMPOSITIONS FOR TREATING HYPERTENSION, ANGINA AND OTHER DISORDERS USING OPTICALLY PURE S(–) NITRENDIPINE

[75] Inventors: Timothy J. Barberich, Concord, Mass.; James W. Young, Palo Alto, Calif.

[73] Assignee: Sepracor Inc., Marlborough, Mass.

[21] Appl. No.: 259,930

[22] Filed: Jun. 15, 1994

Related U.S. Application Data

[63] Continuation of Ser. No. 957,200, Oct. 6, 1992, abandoned, which is a continuation-in-part of Ser. No. 492,647, Mar. 13, 1990, Pat. No. 5,190,962.

[51] Int. Cl.$^6$ .................................................... A61K 31/44
[52] U.S. Cl. ........................................................... 514/356
[58] Field of Search .............................................. 514/356

[56] References Cited

U.S. PATENT DOCUMENTS

| | | | |
|---|---|---|---|
| 3,799,934 | 3/1974 | Meyer et al. | 260/294.8 G |
| 3,799,936 | 3/1974 | Meyer et al. | 260/295.5 R |
| 3,932,645 | 1/1976 | Meyer et al. | 424/266 |
| 3,932,646 | 1/1976 | Meyer et al. | 424/266 |
| 4,145,432 | 3/1979 | Sato | 424/266 |
| 4,582,840 | 4/1986 | Garthoff et al. | 514/213 |
| 4,707,486 | 11/1987 | Flockerzi et al. | 514/318 |
| 4,724,141 | 2/1988 | Schmidt et al. | 424/80 |
| 4,975,440 | 12/1990 | Flockerzi et al. | 514/318 |
| 5,039,674 | 8/1991 | Fujikena et al. | 514/212 |
| 5,051,433 | 9/1991 | Stoltefuss et al. | 514/356 |

FOREIGN PATENT DOCUMENTS

WO90/09376  8/1990  WIPO.

OTHER PUBLICATIONS

Shibanuma, T. et al., "Synthesis of Optically Active 2-(N-Benzyl-N-methylamino) ethyl Methyl 2,6-Dimethy-4-(m-nitrophenyl)-1,4-dihydropyridine-3, 5-dicarboxylate (Nicardipine)," Chem. Pharm. Bull., 28(9):2809-2812 (1980).
Chemical Abstract, 98:317g (1983).
Thomas, G. et al., "Action of dihydropyridine Ca-channel-modulators on isolated heart preparations," Cardiologia, 32(4):1047-1052 (1987).
Maan, A. C. et al. "Analysis of the Properties of Binding of Calcium-Channel Activators and Inhibitors to Dihydropyridine Receptors in Chick Heart Membranes," Circulation Research, 61(3):379-388, 1987.
Rampe, D. et al., "Comparative aspects and temperature dependence of [$^3$H]1,4-dihydropyridine Ca$^{2+}$ channel antagonist and activator binding to neuronal and muscle membrane," Canadian Journal Physiology Pharmacology, 65(7):1452-1460 (1987).
Yatani, A. "Effects of dihydropyridine calcium channel modulators on carciac sodium channels," Am. J. Physiol. 254 (Heart Circ. Pyysiol. 23) H140-H147 (1989).
Soons, P. A. et al., "Oral absorption profile of nitrendipine in healthy subjects: a kinetic and dynamic study," Br. J. Clin. Pharm. 27:179-189 (1989).

Saha, J. K. et al., "Analysis of the effects of (–) and (+) isomers of the 1,4-dihydropyridine calcium channel agonist BAY k 8644 on postrest potentiation in the canine ventricular muscle," Canadian Journal Physiology & Pharmacology, 67(7):788-794 (1989).
Mörike, K. et al., "221 Hämodynamische und biochemische Wirkungen der Nitrendipin-Enantiomere," Klin Wochenschr 67 (Suppl. XVI): 120-121 (1989).
Mikus, G. et al., "Pharmacokinetics, Hemodynamic and Biochemical Effects of the Nitrendipine Enantiomers," Euv. J. Clin. Pharmac. 36(Suppl) A179 (1989).
Soons, P. A. et al., "Stereoselective kinets of Felopine and Nitrendipine in Man," Clin. Pharmacol. Ther. p. 158 Abstract No. PII-40 (1990).
Soons, P. A. et al., "Enantioselective determination of felodipine and other chiral dihydropyridine calcium entry blockers in human plasma," Journal of Chromatography Biomedical Applications, 528:343-356 (1990).
Eltze, M. et al. "Stereoselective Inhibition of Thromboxane-induced Coronary Vasoconstriction by 1,4-Dihydropyridine Calcium Channel Antagonists," Chirality 2:233-240 (1990).
Okamoto, Y. et al. "Optical resolution of dihydropyridine enantiomers by high-performance liquid chromatography using phenylcarbamates of polysaccharides as chiral stationary phase," Journal of Chromatography, 513:375-378 (1990).
O'Neill, S. K. et al., "Comparative Studies With Enantiomers of Dihydropyridine Ligands Suggests That There Are Multiple Binding Sites Associated With The Calcium Channel," Proc. West. Pharmacol. Soc., 33:235-241 (1990).
Soons, P. A. et al., "Stereoselective pharmcokinetics of oral and intravenous nitrendipine in healthy male subjects," Br. J. Clin. Pharmac., 32, 11-16 (1991).
Soons, P. A. et al., "Grapefruit juice and cimetidine inhibit stereoselective metabolism of nitrendipine in humans," Pharmacokinetics and Drug Disposition, 50(4):394-403 (1991).
Mast, V. et al. "Use of pesudoracemic nitrendipine to elucidate the metabolic steps responsible for stereoselective disposition of nitrendipine enantiomers," Br. J. Clin. Pharmac., 33:51-59 (1992).
Zernig and Glossman, "A novel 1,4-dihydropyridine-binding site on mitochondrial membranes from guinea-pig heart, liver and kidney", Biochem. J 253: 49-58 (1988).

*Primary Examiner*—Marianne M. Cintins
*Assistant Examiner*—William R. A. Jarvis
*Attorney, Agent, or Firm*—Pennie & Edmonds

[57] ABSTRACT

Methods and compositions are disclosed utilizing the optically pure S(–) isomer of nitrendipine. This compound is a potent drug for the treatment of hypertension while avoiding the concomitant liability of adverse effects associated with the administration of the racemic mixture of nitrendipine. The S(–) isomer of nitrendipine is also useful for the treatment of angina and such other conditions as may be related to the activity of S(–) nitrendipine as a calcium channel antagonist without the concomitant liability of adverse effects associated with the racemic mixture of nitrendipine.

33 Claims, No Drawings

METHODS AND COMPOSITIONS FOR TREATING HYPERTENSION, ANGINA AND OTHER DISORDERS USING OPTICALLY PURE S(−) NITRENDIPINE

This is a continuation of application Ser. No. 07/957,200, filed Oct. 6, 1992, now abandoned, which is a continuation-in-part of application Ser. No. 07/492,647, filed Mar. 13, 1990 now U.S. Pat. No. 5,190,962, each of which is incorporated by reference herein in its entirety.

TABLE OF CONTENTS

1. TECHNICAL FIELD
2. BACKGROUND OF THE INVENTION
   2.1. Steric Relationship and Drug Action
   2.2. Pharmacologic Action
3. SUMMARY OF THE INVENTION
4. DETAILED DESCRIPTION OF THE INVENTION
5. EXAMPLES
   5.1. Example 1
   5.2. Example 2
   5.3. Example 3
   5.4. Example 4
   5.5. Example 5
   5.6. Example 6
   5.7. Example 7
   5.8. Example 8

1. TECHNICAL FIELD

This invention relates to novel compositions of matter containing optically pure S(−) nitrendipine. These compositions possess potent activity in treating both systolic and diastolic hypertension while avoiding adverse effects including but not limited to insulin resistance, edema of the extremities, headache, dizziness, flushing and weakness which are associated with administration of the racemic mixture of nitrendipine. Additionally, these novel compositions of matter containing optically pure S(−) nitrendipine are useful in treating angina and such other conditions as may be related to the activity of S(−) nitrendipine as a calcium channel antagonist including but not limited to cerebral ischemia, cerebral disorders, arrhythmias, cardiac hypertrophy, coronary vasospasm, myocardial infarction, renal impairment and acute renal failure—while avoiding the adverse effects associated with administration of the racemic mixture of nitrendipine. Also disclosed are methods for treating the above-described conditions in a human while avoiding the adverse effects that are associated with the racemic mixture of nitrendipine, by administering the optically pure S(−) isomer of nitrendipine to said human.

2. BACKGROUND OF THE INVENTION

2.1. Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the β-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been thought to be a potent teratogen.

The active compound of the present invention is the S(−) isomer of the compound nitrendipine, which is described in U.S. Pat. No. 3,799,934. Chemically, this compound is the S(−) isomer of 1,4-dihydro-2,6-dimethyl-4-(3-nitrophenyl)-3,5-pyridinedicarboxylic acid ethyl methyl ester or ethyl 1,4-dihydro-5-(acetoxycarbonyl)-2,6-dimethyl-4-(3-nitrophenyl)-3-pyrindinecarboxylate. This isomer will hereinafter be referred to as S(−) nitrendipine. The terms "S(−) nitrendipine" and "S(−) isomer of nitrendipine" as used herein includes substantially optically pure S(−) nitrendipine as well as optically pure S(−) nitrendipine. Further, these terms as used herein refers to any biologically acceptable form thereof, such as a salt or ester of this compound.

2.2. Pharmacologic Action

Nitrendipine is a drug belonging to the general class of compounds known as dihydropyridine calcium channel blockers. This class of drugs has the property of inhibiting the transmembrane influx of calcium ions into cardiac and smooth muscle cells. The contractile processes of cardiac and vascular smooth muscle cells are dependent upon the movement of extracellular calcium ions into these cells through specific ion channels. Nitrendipine relaxes coronary vascular smooth muscle, and exerts anti-hypertensive activity at drug levels which cause little or no weakening of cardiac contractility.

Nitrendipine is presently administered and is available commercially only as the 1:1 racemic mixture. That is, it is available as a mixture of optical isomers, called enantiomers. As stated above, enantiomers are structurally identical compounds which differ only in that one isomer is a mirror image of the other and the mirror images cannot be superimposed. This phenomenon is known as chirality.

Dihydropyridine calcium channel blockers are also known as calcium antagonists. The concept of a specific mechanism of pharmacologic action related to the antagonism of calcium movement in the process of excitation-contraction was suggested by Fleckenstein et. al. See *Calcium Antagonism in Heart and Smooth Muscle:Experimental Facts and Therapeutic Prospects*, New York, Wiley, 1983. (See also Swamy, V. and D. Triggle, *Modern Pharmacology*, 2nd. Ed., Craig and Stitzel, Eds., Little, Brown and Co., Boston, 1986, Chapt. 26, 373–380; and Triggle, D. J., and R. A. Janis, *Ann. Rev. Pharm. and Tox.* 27: 347–369, 1987). Many of the currently available calcium antagonists appear to antagonize the entry of calcium through voltage dependent channels in the plasma membrane of cells. The pharmacologic class of calcium antagonists consists of chemically diverse compounds. Given the structural heterogeneity of the class it is likely that the pharmacological action involves more than one site or mechanism of action.

Nitrendipine is one of a series of dihydropyridine calcium antagonists. Its ability to block calcium channels in smooth muscle produces peripheral vasodilation resulting in decreases in both systolic and diastolic blood pressure in hypertensive animals and humans.

With regard to the enantiomers of nitrendipine, these are disclosed in Mikus et al. *Eur. J. Clin. Pharmac.* 36 (Suppl.):A179 (1989). This abstract reports that S(−) nitrendipine alone is responsible for the pharmacological effects observed in six healthy humans. The abstract further alleges that racemic nitrendipine exhibits stereoselective first pass metabolism with a possible interaction of the enantiomers when it is administered as a racemate. However, O'Neill et al. *Proc. West Pharmacol. Soc.* 33: 235–241 (1990) states that [$^3$H]-nitrendipine is a racemic mixture of two enantiomers with only minimal difference, <5 fold, in their affinity for dihydropyridine (DHP) receptors. Moreover, Soons et al. *Clin. Pharmacol. Ther.* 47(2): 158 (1990) report a marked difference in the AUC of the enantiomers of nitrendipine, which they report is most likely due to stereoselective first-pass metabolism. Furthermore, Eltze et al. *Chirality* 2:233–240 (1990) report that the enantiomers of nitrendipine effectively inhibit vasoconstriction due to the TxA$_2$-mimetic U-46619 in guinea pig Langendorff hearts, displace (+) [$^3$H] isradipine from calcium channel-binding sites in guinea pig skeletal muscle T-tubule membranes, and decrease blood pressure in SHR with a similar rank order of potency.

The racemic mixture of nitrendipine is presently used primarily as an antihypertensive agent, and it is generally taken orally as a once-daily therapy. Pharmacologic management of hypertension is generally directed to the normalization of altered hemodynamic parameters, and many drugs and drug classes, either as monotherapy or in combination treatment, can reduce and control elevated blood pressure.

Furthermore, the racemic mixture of nitrendipine is useful in treating other disorders such as angina pectoris. Angina pectoris is a clinical syndrome reflecting myocardial ischemia. A condition where cardiac work or myocardial oxygen demand exceeds the ability of the coronary arterial vascular system to supply oxygen results in myocardial ischemia, which may cause either a painful angina attack or an angina attack that is not accompanied by pain (silent ischemia). Under extreme circumstances, the lack of oxygen may cause a myocardial infarction or cardiac arrhythmias. The treatment of angina is directed to the underlying disease, usually atherosclerosis, or to drugs which either reduce myocardial oxygen demand or improve oxygen supply. Calcium antagonists such as nitrendipine have been particularly useful in treating vasospastic angina, the angina of effort, and the unstable angina, due to the effect of the calcium channel antagonist on cardiac and vascular smooth muscle.

Nitrendipine may be useful in the treatment of cerebral ischemia. Cerebral ischemia, often the result of atherosclerotic disease or hypertension, results from insufficient cerebral circulation. Under normal circumstances, an extensive collateral circulation ensures adequate blood flow. However, cerebral ischemia may result from either an intra- or extracranial interruption of arterial blood flow caused by atherosclerosis or arterial vasoconstriction. If interruption is transient, the cause is usually arterial vasoconstriction and a calcium antagonist may be of therapeutic value. If the ischemia lasts for a more extended period, it is usually caused by carotid or cerebral atherosclerosis that may be accompanied by a vasospecific condition that can be treated with a vasodilating calcium antagonist.

Because of its activity as a calcium channel antagonist, nitrendipine may also be useful in treating cardiac arrhythmias. Cardiac arrhythmias represent a broad, complex group of electrophysiologic disorders that effects the mechanical properties of the heart and vasculature, altering normal cardiac rhythm, function and output. Normal cardiac rhythm originates as a calcium dependent action potential within the sinoatrial node, propagates through the atria and passes as a calcium dependent potential through the atrioventricular node and along the purkinje fibers into the ventricles of the heart. Adequate automaticity and conduction are necessary elements of normal functional heart beat. Calcium antagonists may be of value in conditions where calcium-related changes in membrane potential and conduction alter normal rhythm and in cases of ischemia-induced cardiac arrhythmias.

Nitrendipine may be useful to treat cardiac hypertrophy. Cardiac hypertrophy can result from excessive workload either due to an obstruction to outflow, termed systolic overload, or to excessive volumes presented to the heart in diastole, termed diastolic overload. Systolic overload results in concentric ventricular hypertrophy, in which there is an increased thickness in the walls of the heart not associated with increased volume. Diastolic overload causes dilation and hypertrophy with an increased blood volume. An inadequate cardiac output results from the heart's failure in systolic or diastolic overload. Calcium channel antagonists dilate peripheral capacitance blood vessels and thereby reduce the amount of blood returning to the heart and the risk for diastolic overload. Calcium antagonists also dilate peripheral resistance blood vessels, thereby reducing blood pressure (cardiac afterload) and the risk for systolic overload.

Myocardial infarction may be precipitated by coronary artery vasospasm or acute coronary thrombosis. Calcium channel antagonists may find utility in the management of myocardial infarction patients due to "direct" anti-ischemic effects or due to their effects on coronary artery vasospasm, blood pressure or other cardiac or vascular functions.

Nitrendipine may be used to treat congestive heart failure. Congestive heart failure can be caused by hypertension, cardiomyopathy, coronary artery disease or valvular heart disease. Congestive failure results in poor cardiac output and elevated left-ventricular diastolic pressure, leading to dyspnea, fatigue, peripheral edema, and coughing. The ability of some calcium antagonists to lower arterial blood pressure by dilating peripheral arteries without having a significant inotropic effect may increase their use in treating congestive heart failure.

Nitrendipine may be of use in treating migraine. Classic migraine typically begins with visual auras followed by severe headaches, often accompanied by nausea and vomiting. Common migraine has similar symptoms without the preceding visual aura. The causes of migraine have been studied intensely, and are still a matter of debate. The most generally accepted cause is an initial cerebral vasoconstriction, followed by a cerebral vasodilatation. Calcium channel antagonists have been used for migraine prophylaxis since they can inhibit the initial vasoconstriction.

Nitrendipine may also be useful for treating Raynaud's phenomenon, which is characterized by vascular spasm of the extremities. These vasospasms can be caused by cold or stress. A pallor or cyanosis is usually present due to severe constriction of the digital arteries. The phenomenon is often seen as a secondary disorder with arterial diseases or connective tissue diseases such as scleroderma, arthritis or lupus erythematosus. Calcium channel antagonists have been shown to be effective in treating Raynaud's phenomenon.

Nitrendipine may be useful in the treatment of asthma and bronchospasm. Symptoms of asthma—coughing, wheezing, and dyspnea—are caused by constriction of tracheobronchial smooth muscle. Asthma attacks can be triggered by antigenic stimuli (pollen, dust) or non-antigenic stimuli (exercise, pollution, infection). The response to these stimuli lead to secretions of chemical mediators that cause smooth muscle contraction. Calcium channel antagonists can cause relaxation of the bronchial smooth muscles and thereby relieve or prevent asthma attacks.

In addition, the racemic mixture of nitrendipine may be useful to treat renal impairment and acute renal failure. Renal impairment and acute renal failure are clinical conditions of diverse etiology, which are associated with an increasing azotemia or urea nitrogen in the blood, and often an oliguria or a diminished volume of urine in relation to fluid intake. The pathophysiology may originate prerenally, manifest as inadequate renal perfusion, due to extracellular fluid volume depletion or cardiac failure. The most common cause of intrinsic renal failure is prolonged renal ischemia. Postrenal azotemia may be associated with obstruction or renal glomerular and tubular dysfunction. Laboratory findings in patients with renal failure often disclose progressive azotemia, acidosis, hyperkalemia, and hyponatremia. Factors aggravating kidney impairment or failure must be specifically treated, including heart failure, obstruction and the like. Moderate or severe hypertension has a deleterious effect on renal function, and management of the hypertension with a variety of drugs including calcium channel antagonists may be useful therapy.

In addition, the racemic mixture of nitrendipine could be useful in the treatment of cognitive disorders. Cognitive disorders include but are not limited to dementia and age-associated memory impairment.

Calcium antagonists such as nitrendipine may also be used for the treatment of ocular (retinal) ischemia, that often is the result of local vasoconstriction.

Many calcium channel antagonists cause significant adverse effects. These adverse effects include but are not limited to tachycardia, orthostatic hypotension, fluid retention and insulin resistance. The administration of the racemic mixture of nitrendipine to a human has been found to cause still other adverse effects. These adverse effects include but are not limited to peripheral edemas, headache, flushing, hot flashes, fatigue, weakness, vertigo, muscle cramps, dizziness and gastrointestinal symptoms.

Thus, it would be particularly desirable to find a compound with the advantages of the racemic mixture of nitrendipine which would not have the aforementioned disadvantages.

3. SUMMARY OF THE INVENTION

It has now been discovered that the optically pure S(−) isomer of nitrendipine is an effective antihypertensive agent for both systolic and diastolic hypertension, particularly in mild to moderate disease and angina, which avoids the adverse effects including but not limited to insulin resistance, edema of the extremities, headache, flushing, weakness and dizziness which are associated with the administration of the racemic mixture of nitrendipine. It has also been discovered that these novel compositions of matter containing optically pure S(−) nitrendipine are useful in treating other conditions as may be related to the activity of S(−) nitrendipine as a calcium channel antagonist, including but not limited to cerebral ischemia, cerebral disorders, arrhythmias, cardiac hypertrophy, coronary vasospasm, myocardial infarction, renal impairment and acute renal failure while avoiding the above-described adverse effects associated with the administration of the racemic mixture of nitrendipine. The present invention also includes methods for treating the above-described conditions in a human while avoiding the adverse effects that are associated with the racemic mixture of nitrendipine by administering the S(−) isomer of nitrendipine to said human.

The present invention relates to a method of treating hypertension in an individual, comprising administering to the individual a therapeutically effective amount of the optically pure S(−) enantiomer of nitrendipine which has anti-hypertensive activity. The optically pure S(−) enantiomer is substantially free of the R(+) enantiomer which lacks or has a lower level of such activity. The present method is useful in treating hypertension while reducing or avoiding undesirable adverse effects, such as insulin resistance, headache, flushing, dizziness, weakness, and peripheral edema which are often associated with administration of a racemic mixture of nitrendipine. In these applications, it is important to have an anti-hypertensive composition which minimize these side effects. A composition containing the optically pure S(−) isomer of nitrendipine having anti-hypertensive activity is particularly useful for this application because the S(−) isomer exhibits both of these desired characteristics.

The present method provides a safe, highly effective method for treating severe hypertension while reducing undesirable adverse effects associated with anti-hypertensive drugs, including the racemic mixture of nitrendipine.

4. DETAILED DESCRIPTION OF THE INVENTION

The present invention relies on the calcium channel blocking activity of the optically pure S(−) enantiomer of nitrendipine to provide enhanced calcium channel antagonist activity, for example, for treatment or prevention of hypertension, while simultaneously avoiding many of the undesirable adverse effects associated with anti-hypertensive drugs including the racemic mixture of nitrendipine. Such effects include but are not limited to insulin resistance, headache, flushing, dizziness, weakness and peripheral edema. In the present method, the optically pure S(−) isomer of nitrendipine which exhibits anti-hypertensive activity is administered alone, or in combination with other drugs in adjunctive treatment to an individual suffering from hypertension.

The present invention encompasses a method of treating hypertension in a human, while avoiding the concomitant liability of adverse effects associated with the racemic mixture of nitrendipine, which comprises administering to a human in need of such antihypertensive therapy, an amount of S(−) nitrendipine or a pharmaceutically acceptable salt thereof, substantially free of its R(+) stereoisomer, said amount being sufficient to alleviate hypertension, but insufficient to cause said adverse effects associated with administration of racemic nitrendipine.

The present invention also encompasses an pharmaceutical composition for the treatment of hypertension in a human in need of antihypertensive therapy, which comprises an amount of S(−) nitrendipine or a pharmaceutically acceptable salt thereof, substantially free of its R(+) stereoisomer, said amount being sufficient to alleviate said hypertension but insufficient to cause adverse effects of racemic nitrendipine. The antihypertensive composition may optionally contain a pharmaceutically acceptable carrier.

The present invention further encompasses a method of treating angina in a human, while avoiding the concomitant liability of adverse effects associated with the administration of racemic nitrendipine, which comprises administering to a human in need of anti-angina therapy, an amount of S(−) nitrendipine, or a pharmaceutically acceptable salt thereof, substantially free of its R(+) stereoisomer, said amount being sufficient to alleviate angina but insufficient to cause said adverse effects associated with administration of racemic nitrendipine.

In addition, the present invention encompasses an pharmaceutical composition for the treatment of a human having angina, which comprises an amount of S(−) nitrendipine or a pharmaceutically acceptable salt thereof, substantially free of its R(+) stereoisomer, said amount being sufficient to alleviate angina but insufficient to cause adverse effects associated with the administration of racemic nitrendipine. The antianginal composition may optionally contain a pharmaceutically acceptable carrier.

A further aspect of the present invention includes a method of treating a condition caused by excessive calcium influx in cells in a human, while avoiding the concomitant liability of adverse effects associated with the administration of racemic nitrendipine, which comprises administering to a human in need of a reduction in excessive calcium influx, an amount of S(−) nitrendipine, or a pharmaceutically acceptable salt thereof, substantially free of its R(+) stereoisomer, said amount being sufficient to alleviate or prevent excessive calcium influx in cells but insufficient to cause said adverse effects associated with the administration of racemic nitrendipine. Conditions caused by excessive calcium influx in cells in a human include, but are not limited to, cerebral ischemia, cerebral disorders such as cognitive disorders including but not limited to Alzheimer's dementia and memory impairment, retinal ischemia, arrhythmias, cardiac hypertrophy, congestive heart failure, coronary vasospasm, migraine, bronchospasm and asthma, Raynaud's phenomenon, myocardial infarction, renal impairment and acute renal failure.

Furthermore, the present invention includes a pharmaceutical composition for treating a condition caused by excessive calcium influx in cells in a human, which comprises an amount of S(−) nitrendipine, or a pharmaceutically acceptable salt thereof, substantially free of its R(+) stereoisomer, said amount being sufficient to alleviate said condition but insufficient to cause adverse effects associated with the administration of racemic nitrendipine. This pharmaceutical composition may optionally contain a pharmaceutically acceptable carrier.

The commercially available racemic mixture of nitrendipine (e.g., a 1:1 racemic mixture of the two enantiomers) demonstrates antihypertensive and antianginal activity; however, this racemic mixture, while offering the expectation of efficacy, causes adverse effects. Utilizing the optically pure S(−) isomer of nitrendipine results in clearer dose-related definitions of efficacy, surprisingly diminished adverse effects, and accordingly, an improved therapeutic index. It is, therefore, more desirable to use the optically pure S(−) isomer of nitrendipine.

The term "adverse effects of racemic nitrendipine" or "adverse effects associated with the racemic mixture of nitrendipine as used herein includes, but is not limited to, cardiovascular effects (including tachycardia and diminished contractility of the heart), insulin resistance, edema of the extremities, headache, dizziness, flushing, fatigue, weakness, vertigo, and muscle cramps.

The term "substantially free of its R(+) stereoisomer" as used herein means that the composition contains a greater proportion or percentage of the S(−) isomer of nitrendipine in relation to the R(+) isomer of nitrendipine, said percentage being based on the total amount of nitrendipine in the composition. In a preferred embodiment the term "substantially free of its R(+) stereoisomer" means that the composition contains at least 90% by weight of S(−) nitrendipine, and 10% by weight or less of R(+) nitrendipine. In the most preferred embodiment the term "substantially free of the R(+) stereoisomer" means that the composition contains at least 99% by weight S(−) nitrendipine, and 1% or less of R(+) nitrendipine. In another preferred embodiment the term "substantially free of its R(+) stereoisomer" as used herein means that the composition contains about 100% by weight of S(−) nitrendipine. The terms "substantially optically pure S(−) isomer of nitrendipine" and "optically pure S(−) isomer of nitrendipine" are also encompassed by the above-described meanings.

The term "a method of treating hypertension" as used herein means providing a normalization to otherwise elevated systolic and/or diastolic blood pressure, and by so doing providing relief from any possible symptoms or other hemodynamic effects caused by the elevated pressure.

The term "a method of treating angina" as used herein means relief from the symptoms of myocardial ischemia, which include, but are not limited to, episodes of precordial pressure, discomfort, or a severe intense, crushing pain which may radiate, and which may be accompanied by changes in respiration, pulse rate, and blood pressure.

The term "a condition caused by excessive calcium influx in cells in a human" includes but is not limited to conditions involving calcium influx in human cell that may be present in smooth muscle, cardiac, and other tissues including lung and brain. These conditions include, but are not limited to, cerebral ischemia, cerebral disorders such as cognitive disorders including Alzheimer's dementia and memory impairment, retinal ischemia, arrhythmias, cardiac hypertrophy, congestive heart failure, coronary vasospasm, migraine, bronchospasm and asthma, Raynaud's phenomenon, myocardial infarction, renal impairment and acute renal failure. The symptoms associated with these disorders include, but are not limited to, the symptoms of precordial discomfort or pain, headache, fatigue, decreased exercise tolerance, syncope, shortness of breath, nausea, lightheadedness, edema, pulmonary congestion, arrhythmia or palpitation, azotemia, and/or oliguria.

Optically pure S(−) nitrendipine can be prepared in a number of ways. Among these methods, the resolution of a racemic mixture of nitrendipine or its precursors and the asymmetric synthesis of nitrendipine or precursors thereof are particularly useful. Resolution of a racemic mixture by fractional crystallization of diastereomeric derivatives or salts is perhaps the most straightforward method for obtaining optically pure S(−) nitrendipine.

Optically active resolving agents are employed in the resolution of these racemic mixtures of the nitrendipine enantiomers which are obtained following synthetic procedures known in the art (See, for example, U.S. Pat. No. 3,799,934.). The resolution of racemates by fractional crystallization of diastereomeric salts formed with such resolving agents is perhaps the most commonly used conventional technique for producing optically pure compounds. See, for example, "Stereochemistry of Carbon Compounds," E. L. Eliel (McGraw-Hill, NY, 1986) and "S. H. Wilen, p. 268, in "Tables of Resolving Agents and Optical Resolutions," E. L. Eliel, Ed., Univ. of Notre Dame Press, Notre Dame, Ind., 1972.

Since nitrendipine is a basic compound, diastereomeric salts suitable for separation by fractional crystallization are readily formed by the addition of chiral acid resolving agents in optically pure form to racemic nitrendipine. Suitable resolving agents for use here include optically pure tartaric acid and its derivatives, camphorsulfonic acid, mandelic acid and derivatives thereof, and other optically active acids. The desired S(−) nitrendipine isomer may be recovered either from the crystallized diastereomer or from the mother liquor, depending on the solubility properties of the particular acid resolving agent employed and depending on the particular acid enantiomer used. The identity of the S(−) nitrendipine isomer so obtained may be confirmed by polarimetry and other analytical methods.

A particular preferred means of obtaining S(−) nitrendipine is based on the fractional crystallization of diastereomeric mixtures formed by basic resolving agents and racemic carboxylic-acid-containing precursors of nitrendipine. See, for example, T. Shibanuma et al., Chem. Pharm. Bull. 28(9): 2809–2812 (1980) (who resolved the structurally related dihydropyridine nicardipine) and M. Eltze et al., Chirality 2: 233–240 (1990) and references cited therein. In particular, S(−) nitrendipine is obtained by means of resolution of the corresponding racemic 4-aryl-1-ethoxymethyl-1,4-dihydro-5-methoxycarbonyl-2,6-dimethylpyridine-3-carboxylic acids by means of crystallization of the diastereomeric salts formed upon addition of basic resolving agents to the racemic precursor—followed by subsequent alkylation and esterification as described in International Patent Applications WO 88/07524 and WO 88/07525, Byk Gulden, 1988. Optically pure cinchonine and cinchonidine salts are basic resolving agents that have proven useful in the resolution of the dihydropyridines including nitrendipine.

The chemical synthesis of the racemic mixture of nitrendipine can be performed by the method described in U.S. Pat. No. 3,799,934 as well as by other means known to those skilled in the art. See, for example, Arrowsmith, J. E. et al., J. Med. Chem., 29: 1696–1702 (1966).

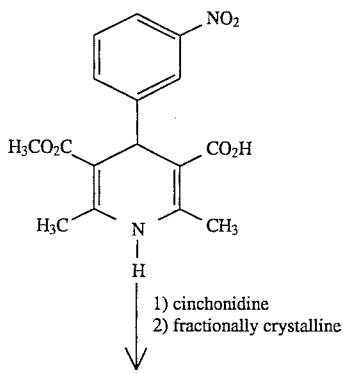

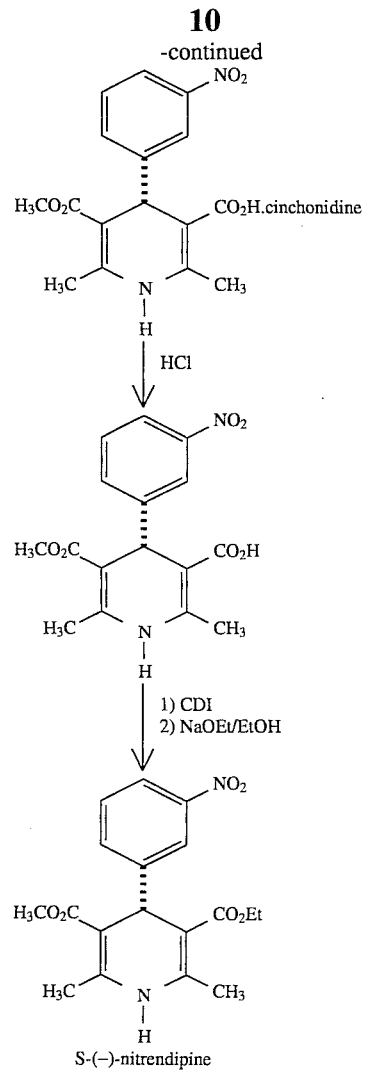

The racemic acid ester is converted to its cinchonidine salt in methanol solution. Upon dilution with water and standing at room temperature, a crystalline precipitate is formed which can be subsequently recrystallized to constant rotation to give the diastereomerically pure cinchonidine salt. Further, the mother liquids from the original crystallization can be reduced in volume and stirred at room temperature, e.g., overnight, to afford a fine precipitate which can also be recrystallized to give the diastereomerically pure cinchonidine salt. The cinchonidine salt is partitioned between ethyl acetate and dilute hydrochloric acid to liberate the enantiomerically pure acid. The acid is then esterified using carbonyldiimidazole (CDI) and ethanolic sodium ethoxide, yielding S(−) nitrendipine.

The magnitude of a prophylactic or therapeutic dose of S(−) nitrendipine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 10 mg to about 180 mg. Preferably, a daily dose range should be between about 20 mg to about 120 mg, while most preferably, a daily dose range should be between about 30 mg to about 90 mg. In managing the patient, the therapy should be initiated at a lower dose and increased depending on the patient's global response. It is further recommended that children and patients over 65 years, and those with impaired renal or hepatic function, initially receive low doses, and that they be titrated based on global response and blood level. It may be necessary to use dosages outside these ranges in some cases as will be apparent to those skilled in the art. Further, it is noted that the clinician or treating physician would know how and when to interrupt, adjust, or terminate therapy in conjunction with individual patient response.

The various terms "an amount sufficient to alleviate hypertension but insufficient to cause said adverse effects associated with the administration of racemic nitrendipine", "an amount sufficient to alleviate angina but insufficient to cause said adverse effects associated with the administration of racemic nitrendipine" "an amount sufficient to alleviate ocular (retinal) ischemia, but insufficient to cause said adverse effects associated with the administration of racemic nitrendipine" and "an amount sufficient to alleviate said condition but insufficient to cause said adverse effects associated with the administration of racemic nitrendipine" wherein said condition includes but is not limited to cerebral ischemia, cerebral disorders, arrhythmias, cardiac hypertrophy, coronary vasospasm, myocardial infarction, renal impairment and acute renal failure, are encompassed by the above described dosage amounts and dose frequency schedule.

In one embodiment of the present method, the optically pure S(−) isomer of nitrendipine is administered to an individual suffering from hypertension. For example, S(−) nitrendipine is administered therapeutically to an individual to reduce or ameliorate hypertension. In another embodiment, optically pure S(−) nitrendipine can be administered prophylactically to reduce the probability of occurrence of hypertension.

Any suitable route of administration may be employed for providing the patient with an effective dosage of (−) nitrendipine. For example, oral, rectal, parenteral, ocular, subcutaneous, intravenous, intramuscular, transdermal, and the like may be employed. Dosage forms include tablets, troches, dispersions, suspensions, solutions, capsules, patches, and the like.

The pharmaceutical compositions of the present invention comprise S(−) nitrendipine as active ingredient, or a pharmaceutically acceptable salt thereof, and may also contain a pharmaceutically acceptable carrier, and optionally, other therapeutic ingredients.

In the methods of the present invention, the optically pure isomer of nitrendipine can be administered along with one or more additional drugs. For example, other anti-hypertensive agents, such as thiazide-type diuretics and beta blockers, can be given with or in close temporal proximity to administration of optically pure nitrendipine. The two (or more) drugs (optically pure S(−) nitrendipine and another drug) can be administered in one composition or as two separate entities. For example, they can be administered in a single capsule, tablet, powder, liquid, etc. or as individual compounds. The components included in a particular composition, in addition to optically pure S(−) nitrendipine, and another drug or drugs, are determined primarily by the manner in which the composition is to be administered. For example, a composition to be administered orally in tablet form can include, in addition to the drugs, a filler (e.g., lactose), a binder (e.g., carboxymethyl cellulose, gum arabic, gelatin), an adjuvant, a flavoring agent, a coloring agent and a coating material (e.g., wax or a plasticizer). A composition to be administered in liquid form can include the combination of drugs and, optionally, an emulsifying agent, a flavoring agent and/or a coloring agent.

The term "pharmaceutically acceptable salts" refers to salts prepared from pharmaceutically acceptable non-toxic acids including inorganic acids and organic acids. Optionally, ester analogues of S(−) nitrendipine may be used in the present invention.

Since the compound of the present invention is basic, salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids. (See Campbell, S. F. et al., U.S. Pat. No. 4,806,557.)

The compositions include compositions suitable for oral, ocular, rectal and parenteral (including subcutaneous, intramuscular, and intravenous) administration, although the most suitable route in any given case will depend on the nature and severity of the condition being treated. The most preferred route of the present invention is the oral route. The compositions may be conveniently presented in unit dosage form, and prepared by any of the methods well known in the art of pharmacy.

In the case where an oral composition is employed, a suitable dosage range for use is from about 10 mg to about 180 mg total daily dose, given as a once daily administration in the morning or in divided doses if required. Preferably, a dose range of between about 20 mg to about 120 mg is given as a once daily administration or in divided doses if required, and most preferably a dose range of from between about 30 mg to about 90 mg is given as a once daily administration or in divided doses if required. Patients may be upward titrated from below to within this dose range to a satisfactory control of symptoms or blood pressure as appropriate.

In practical use, S(−) nitrendipine can be combined as the active ingredient in intimate admixture with a pharmaceutical carrier according to conventional pharmaceutical compounding techniques. The carrier may take a wide variety of forms depending on the form of the preparation desired for administration, e.g., oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets) with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference. Further, the compounds of the present invention are particularly suitable for administration by standard means for transdermal delivery as known to those skilled in the art. Moreover, these compounds can be administered by means described in U.S. Pat. Nos. 4,992,445 and 5,001,139 which are hereby incorporated by reference.

For the treatment of ocular (retinal) ischemia, the compounds of the present invention may be administered orally, as described above, or in the form of liquid eyedrops, preferably containing from about 0.2 to about 10 mg active ingredient per drop.

Pharmaceutical compositions of the present invention suitable for oral administration may be presented as discrete units such as capsules, cachets, or tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, and/or surface active or dispersing agent. Molded tablets may be made by molding in a suitable machine a mixture of the powdered compound moistened with an inert liquid diluent. Desirably, each tablet contains from about 5 mg to about 20 mg of the active ingredient, and each cachet or capsule contains from about 5 mg to about 20 mg of the active ingredient, S(−) nitrendipine. Most preferably, the tablet, cachet or capsule contains either one of three dosages, 5 mg, 10 mg and 20 mg (as scored tablets, the preferable dose form) of the active ingredient.

The invention is further defined by reference to the following examples describing in detail the testing and preparation of the compositions of the present invention. It will be apparent to those skilled in the art, that many modifications, both to materials and methods, may be practiced without departing from the purpose and interest of this invention.

5. EXAMPLES

5.1. Example 1

Vascular Selectivity Studies

The relative potency of optically pure S(−) nitrendipine and racemic nitrendipine as calcium channel antagonists and negative inotropic agents are determined by a pharmacological study. Evaluation of these compounds and others in in vitro test systems provide results, from which the vascular selectivity of a particular compound can be assessed. Calcium channel antagonist activity of the compounds as a function of their molar concentration can be evaluated by measuring their inhibition of the calcium-induced contraction of strips of rat aorta immersed in a bath of Krebs-Henseleit buffer containing 45 mM $K^+$ and no $Ca^{2+}$. In the presence of various concentrations of the antagonists, inhibition would occur in the contraction of this isolated tissue preparation in response to the addition of calcium chloride. Antagonists may be compared by examining the molar concentration of compounds inhibiting the calcium-induced contraction by 50%.

As an index of cardiac depression, negative inotropic activity may be comparably assessed using isolated heart preparations of adult rats. The tissues are prepared and perfused in vitro with Krebs-Henseleit buffer solution, with the activity of the calcium channel antagonists evaluated as a function of their concentration. The compounds are tested for their ability to alter cardiac contraction. Relative potency is calculated from the $IC_{25}$ values of the compounds, i.e., the concentration required to depress contraction by 25%.

5.2. Example 2

Radioligand Binding Studies

Hind limb skeletal muscles from rats or guinea pigs are minced and homogenized. After filtration and repeated centrifugation, the pellet is homogenized and diluted in a Tris buffer to a protein concentration of 1–3 mg/ml. Volumes of this suspension containing 3–10 μg protein are incubated in the presence of a fixed concentration of 0.2 to 0.5 nM (+)-[$^3$H]-isradipine or a similar radioactive ligand and increasing concentrations of racemic nitrendipine, S(−) nitrendipine or R(+) nitrendipine. After 1 hour incubation, the bound and free radioactivity is measured in a scintillation counter and the affinity of the test compounds to the receptors is calculated.

5.3. Example 3

Effects on Coronary Muscular Resistance in the Guinea Pig Langendorff Heart Preparation Male guinea pigs weighing between 400 and 450 g are killed by cervical dislocation. The hearts are removed and perfused with Krebs-Henseleit solution at constant pressure (60 cm water) by means of retrograde cannulation of the aorta in a Langendorff apparatus. The Krebs-Henseleit solution, consisting of 118.0 mM NaCl, 4.7 mM KCl, 5.5 mM $CaCl_2$, 1.2 mM $MgSO_4$, 25.0 mM $NaHCO_3$ and 5.0 mM glucose, is prewarmed to 37° C. and gassed with a mixture of 95% oxygen/5% carbon dioxide. A balloon catheter connected to a pressure transducer is placed in the left ventricle via the left atrium and is preloaded to a pressure of 40 mm Hg. Coronary perfusate flow is measured continuously, and changes in heart rate and left ventricular contractility are also monitored continuously.

Each experiment consists of a 30 minute equilibrium period during which coronary flow is stabilized at 9–12 ml/min. Following this period, a vasoconstrictor is injected 3 times at 40 minute intervals into the cannulated aorta. This dose of U-46619 (9,11-methanoepoxy-$PGH_2$) evokes approximately a 75% decrease in coronary flow within 30–40 sec, and the effect is fully reversible after 20–25 min continuous perfusion. Racemic nitrendipine, S(−) nitrendipine or R(+) nitrendipine dissolved in dimethyl sulfoxide or the vehicle are injected in increasing concentrations prior to further U-46619 injections.

The mean decrease in coronary flow obtained with three consecutive injections of U-46619 in the absence of the test substance is taken to be 100% and the percent inhibition of this effect in the presence of increasing concentrations of the test drugs is calculated. Complete individual dose-response curves for each test drug are generated in five hearts, enabling the calculation of the dose for the half-maximal antivasoconstrictor effect ($ID_{50}$).

5.4. Example 4

Antihypertensive Efficacy in Spontaneously Hypertensive Rats

Male spontaneously hypertensive rats (300–350 g) are anesthetized, and polyethylene catheters are implanted in the abdominal aorta via a femoral artery, and in the abdominal vena cava via a femoral vein. The arterial catheters are connected to pressure transducers by means of an intraflow device, flushing the catheters with 3 ml/hr. Mean arterial pressures are derived electronically from the blood pressure wave. Mean pretreatment values of mean arterial pressure are in the range of 160–220 mm Hg. Doses of racemic nitrendipine, S(−) nitrendipine and R(+) nitrendipine, or of the solvent vehicle, are injected into the venous catheter. Responses in mean arterial pressure to the respective drug or solvent are registered and the relative potencies of the test compounds are calculated.

5.5. Example 5

Cardiovascular

Calcium Antagonism, Guinea Pig Ileum (in vitro):

Test substance (3 µg/ml) inhibition of the contractile response of the $K^+$-depolarized isolated guinea pig ileal segment, bathed in Ca-free physiological salt solution at 37° C., to added calcium (20 µg/ml of CaCl), indicates calcium antagonist activity.
Reference Agents ($ED_{100}$, µg/ml):

| atropine | >2 | isoxuprine | 4 |
| cinnazrizine | 1 | mepyramine | >5 |
| cyproheptadine | 0.025 | nifedipine | 0.001 |
| diltiazem | 0.01 | papaverine | 4 |
| diphenhydramine | 1 | promethazine | 0.25 |
| flunarizine | 0.1 | propranolol | 4 |
| ipratropium bromide | >2 | verapamil | 0.01 |

5.6. Example 6

Studies on Insulin Resistance

Insulin is a hormone that activates various biochemical processes in the body, the most well known being facilitation of glucose transport over cell membranes and activation of cell growth. The development of insulin resistance is common both in diabetics and nondiabetics, but it is only the glucose transport system that develops resistance to insulin. To compensate for the impaired glucose transport, the normal body produces more insulin and the diabetic patient has to inject higher doses of insulin. Since insulin also is a growth hormone, the increased insulin concentration induces an accelerated growth of atherosclerotic lesions and increased risk for cardiovascular morbidity and mortality.

Several calcium antagonists of the dihydropyridine class, such as nifedipine, are known to make the insulin resistance worse, while other blood-pressure-lowering agents, such as captopril, have a beneficial effect by decreasing insulin resistance. The present studies are performed in old, spontaneously hypertensive rats, which are known to develop insulin resistance. Racemic nitrendipine, S(−) nitrendipine, and R(+) nitrendipine are studied for their effects on glucose transport, insulin plasma concentration and arterial blood pressure.

5.7. Example 7

Oral Formulation

Capsules:

| Formula | Quantity per capsule in mg. | | |
|---|---|---|---|
| | A | B | C |
| Active ingredient S(−) Nitrendipine | 5.0 | 10.0 | 20.0 |
| Lactose | 79.0 | 74.0 | 64.0 |
| Corn Starch | 15.0 | 15.0 | 15.0 |
| Magnesium Stearate | 1.0 | 1.0 | 1.0 |
| Weight | 100.0 | 100.0 | 100.0 |

The active ingredient, S(−) nitrendipine, lactose, and corn starch are blended until uniform; then the magnesium stearate is blended into the resulting powder. The resulting mixture is encapsulated into suitably sized two-piece hard gelatin capsules.

5.8. Example 8

Oral Formulation

Tablets:

| Formula | Quantity per capsule in Gm. | | |
|---|---|---|---|
| | A | B | C |
| Active ingredient S(−) Nitrendipine | 5.0 | 10.0 | 20.0 |
| Lactose | 178.5 | 173.5 | 163.5 |
| Corn Starch | 15.0 | 15.0 | 15.0 |
| Magnesium Stearate | 1.5 | 1.5 | 1.5 |
| Compression Weight | 200.0 | 200.0 | 200.0 |

The active ingredient, S(−) nitrendipine, is sieved through a suitable sieve and blended with lactose, starch, and pregelatinized maize starch. Suitable volumes of purified water are added and the powders are granulated. After drying, the granules are screened and blended with the magnesium stearate. The granules are then compressed into tablets using 7 mm diameter of punches.

Tablets of other strengths may be prepared by altering the ratio of active ingredient to lactose or the compression weight and using punches to suit.

What is claimed is:

1. A method for treating hypertension in a human, while avoiding the concomitant liability of adverse effects associated with administration of racemic nitrendipine, which comprises administering to a human in need of antihypertensive therapy, an amount of S(−) nitrendipine, or a pharmaceutically acceptable salt thereof, substantially free of its R(+) stereoisomer, said amount being sufficient to alleviate hypertension but insufficient to cause said adverse effects of racemic nitrendipine.

2. The method of claim 1 wherein S(−) nitrendipine is administered by intravenous infusion, by transdermal delivery, or orally as a tablet or a capsule.

3. The method of claim 2 wherein the amount administered is from about 10 mg to about 180 mg daily.

4. The method of claim 3 wherein the amount administered is from about 20 mg to about 120 mg.

5. The method of claim 4 wherein the amount administered is from about 30 mg to about 90 mg.

6. The method of claim 1 wherein the amount of S(−) nitrendipine or a pharmaceutically acceptable salt thereof is greater than approximately 90% by weight of the total weight of nitrendipine.

7. The method of claim 1 wherein the amount of S(−) nitrendipine or a pharmaceutically acceptable salt thereof, substantially free of its R(+) stereoisomer, is administered together with a pharmaceutically acceptable carrier.

8. The method according to claim 1 wherein S(−) nitrendipine is administered as a hydrochloride salt.

9. The method according to claim 1 wherein said S(−) nitrendipine is administered from one to four times a day.

10. The method according to claim 9 wherein said S(−) nitrendipine is administered once a day.

11. A method of treating angina in a human, while avoiding the concomitant liability of adverse effects associated with administration of racemic nitrendipine, which comprises administering to a human in need of anti-angina therapy, an amount of S(−) nitrendipine, or a pharmaceutically acceptable salt thereof, substantially free of its R(+) stereoisomer, said amount being sufficient to alleviate angina but insufficient to cause said adverse effects associated with the administration of racemic nitrendipine.

12. The method of claim 11 wherein S(−) nitrendipine is administered by intravenous infusion, by transdermal delivery, or orally as a tablet or a capsule.

13. The method of claim 12 wherein the amount administered is from about 10 mg to about 180 mg.

14. The method of claim 13 wherein the amount administered is from about 20 mg to about 120 mg.

15. The method of claim 14 wherein the amount administered is from about 30 mg to about 90 mg.

16. The method of claim 11 wherein the amount of S(−) nitrendipine or a pharmaceutically acceptable salt thereof is greater than approximately 90% by weight of the total weight of nitrendipine.

17. The method of claim 11 wherein the amount of S(−) nitrendipine or a pharmaceutically acceptable salt thereof, substantially free of its R(+) stereoisomer, is administered together with a pharmaceutically acceptable carrier.

18. The method according to claim 11 wherein S(−) nitrendipine is administered as a hydrochloride salt.

19. The method according to claim 11 wherein S(−) nitrendipine is administered from one to four times a day.

20. The method according to claim 19 wherein S(−) nitrendipine is administered once a day.

21. A method of treating a condition caused by excessive calcium influx in cells in a human, while avoiding the concomitant liability of adverse effects associated with administration of racemic nitrendipine, which comprises administering to a human in need of treatment of a condition caused by excessive calcium influx in human cells, an amount of S(−) nitrendipine, or a pharmaceutically acceptable salt thereof, substantially free of its R(+) stereoisomer, said amount being sufficient to alleviate said condition but insufficient to cause said adverse effects associated with the administration of racemic nitrendipine.

22. The method according to claim 21 wherein said condition caused by excessive calcium influx in cells in a human is selected from the group consisting of cerebral ischemia, cerebral disorders, cognitive disorders, Alzheimer's dementia, memory impairment, ocular (retinal) ischemia, arrhythmias, cardiac hypertrophy, congestive heart failure, coronary vasospasm, migraine, bronchospasm and asthma, Raynaud's phenomenon, myocardial infarction, renal impairment and acute renal failure.

23. The method of claim 21 wherein S(−) nitrendipine is administered by intravenous infusion, by transdermal delivery, ocular administration, or orally as a tablet or a capsule.

24. The method of claim 23 wherein the amount administered is from about 10 mg to about 180 mg.

25. The method of claim 24 wherein the amount administered is from about 20 mg to about 120 mg.

26. The method of claim 25 wherein the amount administered is from about 30 mg to about 90 mg.

27. The method of claim 21, wherein the amount of S(−) nitrendipine or a pharmaceutically acceptable salt thereof is greater than approximately 90% by weight the total amount of nitrendipine.

28. The method of claim 21 wherein the amount of S(−) nitrendipine or a pharmaceutically acceptable salt thereof, substantially free of its R(+) stereoisomer is administered together with a pharmaceutically acceptable carrier.

29. The method according to claim 21 wherein said S(−) nitrendipine is administered as a hydrochloride salt.

30. The method according to claim 21 wherein said S(−) nitrendipine is administered from one to four times a day.

31. The method according to claim 30 wherein said S(−) nitrendipine is administered once a day.

32. The method according to claim 21 wherein S(−) nitrendipine is administered in the form of an eyedrop solution.

33. The method according to claim 32 wherein the amount administered is from about 0.2 mg to about 10 mg per eyedrop.

* * * * *